(12) United States Patent
Haque et al.

(10) Patent No.: US 8,706,427 B2
(45) Date of Patent: Apr. 22, 2014

(54) METHOD FOR RAPIDLY APPROXIMATING SIMILARITIES

(75) Inventors: Imran Haque, Woodside, CA (US); Vijay Pande, Los Altos, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 311 days.

(21) Appl. No.: 13/035,961

(22) Filed: Feb. 26, 2011

(65) Prior Publication Data

US 2011/0213567 A1     Sep. 1, 2011

Related U.S. Application Data

(60) Provisional application No. 61/339,090, filed on Feb. 26, 2010.

(51) Int. Cl.
*G06F 19/00*     (2011.01)

(52) U.S. Cl.
USPC .......................................................... 702/32

(58) Field of Classification Search
USPC .......................................................... 702/32
See application file for complete search history.

(56) References Cited

U.S. PATENT DOCUMENTS

| | | | |
|---|---|---|---|
| 7,191,106 B2 * | 3/2007 | Minor et al. | 703/2 |
| 7,219,020 B1 * | 5/2007 | Hull et al. | 702/27 |
| 8,515,684 B2 * | 8/2013 | Boyer et al. | 702/19 |

* cited by examiner

*Primary Examiner* — Bryan Bui

(74) *Attorney, Agent, or Firm* — Guadalupe M. Garcia

(57) ABSTRACT

Methods and algorithms are presented that implement linear algebraic techniques for rapidly estimating chemical similarities for several popular measures. The methods of the present invention reflect source similarity measures for both Tanimoto calculation and rank ordering. After a precalculation step on a database, the methods of the present invention afford several orders of magnitude of speedup in database screening. The present invention also provides an asymptotic speedup for large similarity matrix construction problems, reducing the number of conventional slow similarity evaluations required from quadratic to linear scaling.

22 Claims, 11 Drawing Sheets

US 8,706,427 B2

METHOD FOR RAPIDLY APPROXIMATING SIMILARITIES

FEDERALLY-SPONSORED RESEARCH OR DEVELOPMENT

This invention was made with Government support under contracts GM062868 awarded by the National Institutes of Health and contracts 0619926 and 0960306 awarded by the National Science Foundation. The Government has certain rights in this invention.

FIELD OF THE INVENTION

The present invention generally relates to the field of cheminformatics. More particularly, the present invention relates to a technique for rapidly approximating chemical similarities.

BACKGROUND OF THE INVENTION

A fundamental problem in cheminformatics is the calculation of similarity between two given molecules. As a consequence, a large variety of similarity techniques exists. These measures have as their underlying information content a variety of molecular properties, including various encodings of molecular substructure, volume, and surface similarity and of electrostatic similarity. While many of the more complicated techniques are able to uncover relevant chemical similarities not found by simpler methods, they are often computationally expensive to evaluate.

Many important algorithms in cheminformatics contain as a critical subroutine these pairwise similarity comparisons. For example, a database search against a single query (without filters) amounts to the evaluation of a similarity measure once for each database molecule. More complicated algorithms, such as those for clustering or network construction, may require the evaluation of a number of similarities quadratic in the size of the database, rather than linear. Evaluation of similarities can be a bottleneck, limiting performance as well as the size of problems that can be considered. While fingerprint-style methods have been developed to approximate these similarity measures, they lack rigorous justifications of their accuracy.

A significant continuing trend in cheminformatics is the increasing size of virtual chemical databases. Public libraries listing known chemical matter, such as PubChem (31 million molecules) and ZINC (34 million molecules), are routinely used in database searches. Continuing advances in both computational power and storage space enable the use of even larger exhaustive and combinatorial databases. GDB13 is an exhaustive database enumerating all 970 million possible compounds composed of 13 or fewer heavy atoms (C, N, O, S, and Cl), according to simple stability and synthesizability criteria. Virtual combinatorial libraries can similarly reach or exceed the $10^9$ molecule mark, even with as few as three or four points of substitution. In the limit, it is believed that as many as $10^{60}$ molecules are potentially synthesizable. The combination of rapidly growing chemical libraries with computationally difficult similarity metrics suggests a need for dramatically faster methods of calculating chemical similarity.

Algorithms for several emerging large-scale problems in cheminformatics have as their rate-limiting step the evaluation of relatively slow chemical similarity measures, such as structural similarity or three-dimensional (3-D) shape comparison.

SUMMARY OF THE INVENTION

In the present disclosure, methods and algorithms are presented that implement linear algebraic techniques for rapidly estimating chemical similarities for several popular measures. The methods of the present invention reflect source similarity measures for both Tanimoto calculation and rank ordering. After a precalculation step on a database, the methods of the present invention afford several orders of magnitude of speedup in database screening. The present invention also provides an asymptotic speedup for large similarity matrix construction problems, reducing the number of conventional slow similarity evaluations required from quadratic to linear scaling.

The present invention describes a mathematical technique that allows extremely rapid approximate evaluation of compound similarity for a variety of different similarity measures. In one application of interest, the calculation of an all-pairs similarity matrix over a large number of compounds, the present invention offers an asymptotic speedup in terms of the number of similarity calculations required from quadratic to linear scaling.

To be described is a mathematical derivation of the methods of the present invention. Also, the accuracy of the present invention at Tanimoto estimation and generalizability to various similarity measures is presented. Also to be described is a method that allows asymptotic speedup (in terms of number of slow similarity evaluations) on the quadratic-scaling problem of similarity matrix construction.

An embodiment of the present invention is called SCISSORS ("SCISSORS Calculates Interpolated Shape Signatures over Rapid Overlay of Chemical Structures (ROCS) Space").

BRIEF DESCRIPTION OF THE DRAWINGS

The following drawings will be used to more fully describe embodiments of the present invention.

DETAILED DESCRIPTION OF THE INVENTION

Figure 1:
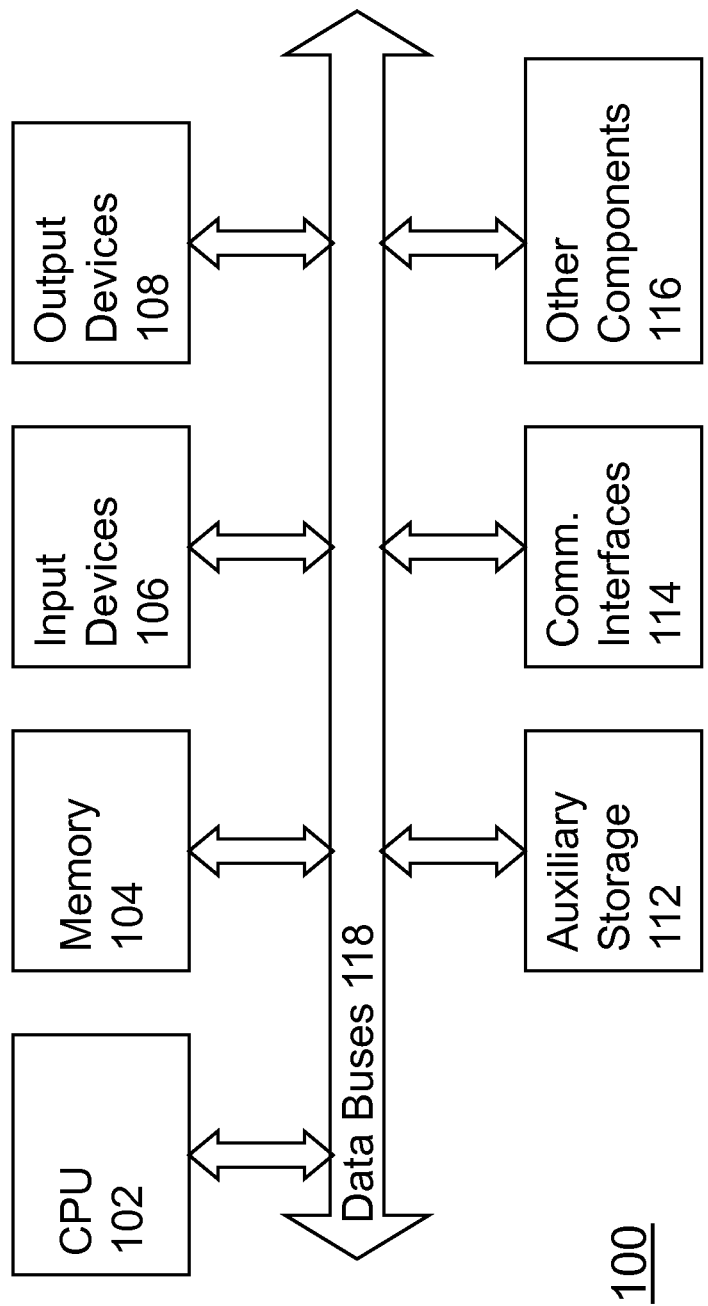
FIG. 1 is a block diagram of a computer system on which the present invention can be implemented.

Among other things, the present invention relates to methods, techniques, and algorithms that are intended to be implemented in a digital computer system 100 such as generally shown in FIG. 1. Such a digital computer is well-known in the art and may include the following.

Computer system 100 may include at least one central processing unit 102 but may include many processors or processing cores. Computer system 100 may further include memory 104 in different forms such as RAM, ROM, hard disk, optical drives, and removable drives that may further include drive controllers and other hardware. Auxiliary storage 112 may also be include that can be similar to memory 104 but may be more remotely incorporated such as in a distributed computer system with distributed memory capabilities.

Computer system 100 may further include at least one output device 108 such as a display unit, video hardware, or other peripherals (e.g., printer). At least one input device 106 may also be included in computer system 100 that may include a pointing device (e.g., mouse), a text input device (e.g., keyboard), or touch screen.

Communications interfaces 114 also form an important aspect of computer system 100 especially where computer system 100 is deployed as a distributed computer system. Computer interfaces 114 may include LAN network adapters, WAN network adapters, wireless interfaces, Bluetooth interfaces, modems and other networking interfaces as currently available and as may be developed in the future.

Computer system 100 may further include other components 116 that may be generally available components as well as specially developed components for implementation of the present invention. Importantly, computer system 100 incorporates various data buses 118 that are intended to allow for communication of the various components of computer system 100. Data buses 118 include, for example, input/output buses and bus controllers.

Indeed, the present invention is not limited to computer system 100 as known at the time of the invention. Instead, the present invention is intended to be deployed in future computer systems with more advanced technology that can make use of all aspects of the present invention. It is expected that computer technology will continue to advance but one of ordinary skill in the art will be able to take the present disclosure and implement the described teachings on the more advanced computers or other digital devices such as mobile telephones or "smart" televisions as they become available. Moreover, the present invention may be implemented on one or more distributed computers. Still further, the present invention may be implemented in various types of software languages including C, C++, and others. Also, one of ordinary skill in the art is familiar with compiling software source code into executable software that may be stored in various forms and in various media (e.g., magnetic, optical, solid state, etc.). One of ordinary skill in the art is familiar with the use of computers and software languages and, with an understanding of the present disclosure, will be able to implement the present teachings for use on a wide variety of computers.

The present disclosure provides a detailed explanation of the present invention with detailed explanations that allow one of ordinary skill in the art to implement the present invention into a computerized method. Certain of these and other details are not included in the present disclosure so as not to detract from the teachings presented herein but it is understood that one of ordinary skill in the art would be familiar with such details.

We now proceed to describe methods and algorithms that implement linear algebraic techniques for rapidly estimating chemical similarities for several popular measures according to the present invention.

One commonality among otherwise diverse techniques to calculate chemical similarity is that, regardless of the underlying method, similarities are often returned as a Tanimoto score. While Tanimotos are often treated simply as real-valued similarities in the range [0,1], they have additional mathematical structure that can be used; this is seen in the definition of the Tanimoto $T_{AB}$ between vectors A and B:

$$T_{AB} \equiv \frac{\langle A, B \rangle}{\langle A, A \rangle + \langle B, B \rangle - \langle A, B \rangle} \quad (1)$$

Equation 1 can be rearranged to obtain an expression for the inner product between two vectors in terms of their Tanimoto:

$$\langle A, B \rangle = \frac{T_{AB}}{1 + T_{AB}} (\langle A, A \rangle + \langle B, B \rangle) \quad (2)$$

Using this equation, the derivation of a method of the present invention proceeds with two assumptions. We first assume that molecules can be represented as vectors in an (unspecified) inner product space. Given this assumption and a similarity measure on two molecules f and g, one can identify these molecules with vectors A and B in equation 2. It then makes sense to ask for the inner product between the two molecules. Since the Tanimoto between the two is known, we must calculate the magnitude of each molecule (e.g., the ⟨A,A⟩ terms).

In the absence of further information, one choice is to set all magnitudes equal to 1 (that is, ⟨A, A⟨=⟩B, B⟩=1); this is equivalent to assuming that all molecules should lie on the surface of a hypersphere of arbitrary dimension N. Alternatively, for certain measures, we have more information and can assign meaningful values to the magnitude.

For the purpose of the derivation of the present invention, we take the magnitudes as given (either from parsimony or knowledge of the measure). This implies that it is possible to calculate the inner product between two molecules given their pairwise Tanimoto score.

We further assume that the inner product space in question is $R^N$, the space of vectors with N real-number coordinates. Under this assumption, it becomes meaningful to try to map molecules to vectors in $R^N$ in such a way as to preserve their inner products. Given a "basis" set of molecules B=$B_1$, ..., $B_k$, k≥N, we require that similarities be computed between all pairs in B. These similarities are then transformed to inner products (using a method appropriate for the measure in question) and placed into a matrix G such that $G_{ij}$ contains the inner product between molecules $B_i$ and $B_j$ (a matrix of this form is known in the statistical literature as a "Gram matrix"). We wish to find a factorization of G of the form $G=MM^T$, where M is an N×N matrix containing the molecule vectors along its rows.

Since the elements of G are constructed from molecular similarities, G is real and symmetric and, therefore, has a spectral decomposition into eigenvectors V and eigenvalues (in diagonal matrix D). From this, the desired factorization follows by algebraic manipulation:

$$G = MM^T \quad (3)$$
$$= VDV^T$$
$$= VD^{1/2}D^{1/2}V^T$$
$$= (VD^{1/2})(VD^{1/2})^T$$
$$M = VD^{1/2}$$

The method described in equation 3 is also used to derive vector coordinates from interpoint distances in multidimensional scaling (MDS). It has several properties which make it an appealing choice relative to other matrix factorizations (such as the Cholesky decomposition, which also finds matrix M such that $G=MM^T$). First, the MDS reconstruction of molecule vectors in N dimensions is guaranteed to most closely approximate the given inner products, in a least-squares sense. Furthermore, the reconstruction dimension can be chosen by sorting the eigenvalues in order of decreasing value and setting to zero all eigenvalues after the first K (for a K-dimensional reconstruction). The method of the present invention is related to a technique known as kernel PCA to be discussed further below.

If the measure described by the inner products in G is a Euclidean metric, then G will be positive semidefinite (i.e., it will have only zero- or positive-valued eigenvalues), and the square root will exist. However, there is no guarantee that a generic molecular similarity measure will be a Euclidean metric (and several popular measures, including ROCS, are not). Because of the optimality properties of MDS, however, the impact that these negative eigenvalues have on the approximation depends on their magnitude relative to the positive eigenvalues. If no negative eigenvalue has magnitude within the top K, then it would not be used in the K-dimensional reconstruction and does not affect the solution.

We demonstrate in our results that for many popular measures, negative eigenvalues are of sufficiently small magnitude that they do not affect the reconstruction and that these non-Euclidean measures can, therefore, be well-approximated by Euclidean inner products. We describe further below a correction factor that can be added to the basic MDS formula to allow interpolation of coordinates associated with negative eigenvalues.

Correction Factors. An issue with our inference procedure is that the optimization procedure (Equation 3) does not respect the vector magnitude assumptions made at the beginning in the first step. In particular, given any molecule A in the basis set with square magnitude $\langle A, A \rangle = x$ and its low-dimensional vector approximation $\tilde{A}$, the approximated square magnitude $\langle \tilde{A}, \tilde{A} \rangle$ will always be smaller than x, because we have ignored the magnitude associated with higher (less significant) dimensions.

As will be shown below when the results are discussed, this loss of magnitude can cause problems with the absolute accuracy of resulting Tanimoto values (though rank orderings are often preserved). One possible strategy for solving this problem would be to replace Equation 3 with a constrained optimization method; however, the simplicity and the ubiquity of implementation of a method based on the spectral decomposition suggest that a procedure to correct the results of the eigenvector decomposition would be useful.

One correction technique is to scale each result vector to force its magnitude to 1. Our testing showed this to be less effective than what we call the slack coordinate method described below. We found such method to improve accuracy and allows for the representation non-Euclidean geometries.

Slack Coordinate Method. Without loss of generality, we consider only the case in which we wish to correct all vector magnitudes to unity. Given real vectors A and B of arbitrary dimension n (i.e., $A, B \in R^n$) with magnitude less than 1, we construct vectors $\tilde{A}$ and $\tilde{B}$ of unity magnitude by augmenting them with one additional "slack" coordinate, as follows:

$$\tilde{A} = [a_0 a_1, \ldots, a_{n-1} a_n]^T \quad (4)$$

$$\tilde{B} = [b_0 b_1, \ldots, b_{n-1} b_n]^T$$

$$\|\tilde{A}\| = \tilde{A}^T \tilde{A} = 1$$

$$\sum_{i=0}^{n} a_i^2 = 1$$

$$a_n^2 = 1 - \sum_{i=0}^{n-1} a_i^2$$

$$a_n = \pm \sqrt{1 - \sum_{i=0}^{n-1} a_i^2}$$

$$b_n = \pm \sqrt{1 - \sum_{i=0}^{n-1} b_i^2}$$

An interesting aspect of this correction is that the slack coordinate is incompletely specified, as the sign is indeterminate. It is possible to derive an analytic correction for the resulting Tanimoto. For convenience, we define variables $k_1$ and $k_2$, corresponding to the numerator and denominator, respectively, of the uncorrected Tanimoto equation:

$$T_{AB} = \frac{\sum_{i=0}^{n-1} a_i b_i}{\sum_{i=0}^{n-1} a_i^2 + \sum_{i=0}^{n-1} b_i^2 - \sum_{i=0}^{n-1} a_i b_i} = \frac{k_1}{k_2} \quad (5)$$

We can then define the corrected Tanimoto in terms of these variables, and simple algebraic transformations allow us to express the correction as a function of the uncorrected Tanimoto and the (uncorrected) magnitudes of A and B:

$$\|A\|^2 = \sum_{i=0}^{n-1} a_i^2 \quad (6)$$

$$\|B\|^2 = \sum_{i=0}^{n-1} b_i^2$$

$$T_{\tilde{A}\tilde{B}} = \frac{\sum_{i=0}^{n} a_i b_i}{\sum_{i=0}^{n} a_i^2 \sum_{i=0}^{n} b_i^2 - \sum_{i=0}^{n} a_i b_i}$$

$$T_{\tilde{A}\tilde{B}} = \frac{k_1 + a_n b_n}{k_2 + a_n^2 + b_n^2 - a_n b_n}$$

$$T_{\tilde{A}\tilde{B}} = \frac{k_1 \pm \sqrt{1 - \|A\|^2} \sqrt{1 - \|B\|^2}}{(2 - k_1) \mp \sqrt{1 - \|A\|^2} \sqrt{1 - \|B\|^2}}$$

$$k_1 = \frac{T_{AB}(\|A\|^2 + \|B\|^2)}{(1 + T_{AB})}$$

$$k_3 = \pm \sqrt{1 - \|A\|^2} \sqrt{1 - \|B\|^2}$$

$$k_4 = k_1 + k_3$$

$$T_{\tilde{A}\tilde{B}} = \frac{k_4}{2 - k_4}$$

Although the sign of the slack coordinate (($\sqrt{1 - \|A\|^2}$ or $\sqrt{1 - \|B\|^2}$ for molecules A and B, respectively) is unspecified, the analytic correction term $k_3$ is not directly dependent on the particular signs of the slack coordinates. Rather, if A and B are real vectors, $k_3$ has sign determined by whether A and B have the same or opposite signs in their slack coordinate. The case in which $k_3$ is always negative (that is, all pairs of vectors A and B have opposite signs in their slack coordinates) turns out to be especially useful. However, this case is not realizable if we restrict our vectors $\tilde{A}$ and $\tilde{B}$ to lie in $R^{n+1}$. As a demonstration, consider three vectors $\tilde{A}$, $\tilde{B}$, and $\tilde{C}$ with slack coordinates $a_n$, $b_n$, and $c_n$. Without loss of generality, let $a_n$ be negative and $b_n$ be positive. For $c_n$ to always have an opposite sign to any molecule to which it was compared, it would have to be positive when molecule C is compared with molecule A and negative when compared to B; this is a contradiction.

Although this style of correction term cannot be implemented with real vectors, by generalizing the vector space, this result is easily understood. The case in which every pair of vectors is associated with a negative correction term $k_3$ corresponds to vectors lying in $R^n \times I$, where the slack coordinate is always positive in sign and purely imaginary n (e.g., in equation 4, let $a_n = i\sqrt{1 - \Sigma_{i=0}^{n-1} a_i^2}$, with $i = \sqrt{-1}$). This interpretation requires that equation 4 be modified so that the Hermitian transpose is used but does not affect the rest of the derivation. The geometry implied by this vector space is known as pseudo-Euclidean, in contrast with the Euclidean geometry of $R^{n+1}$, and has the capability to represent curved spaces. In particular, imaginary coordinates of this form can be used to represent the curved dimensions induced by negative eigenvalues in the Gram matrix. The slack coordinate correction, by generalizing from real to complex vectors, allows approximation of non-Euclidean distance measures.

Figure 2:
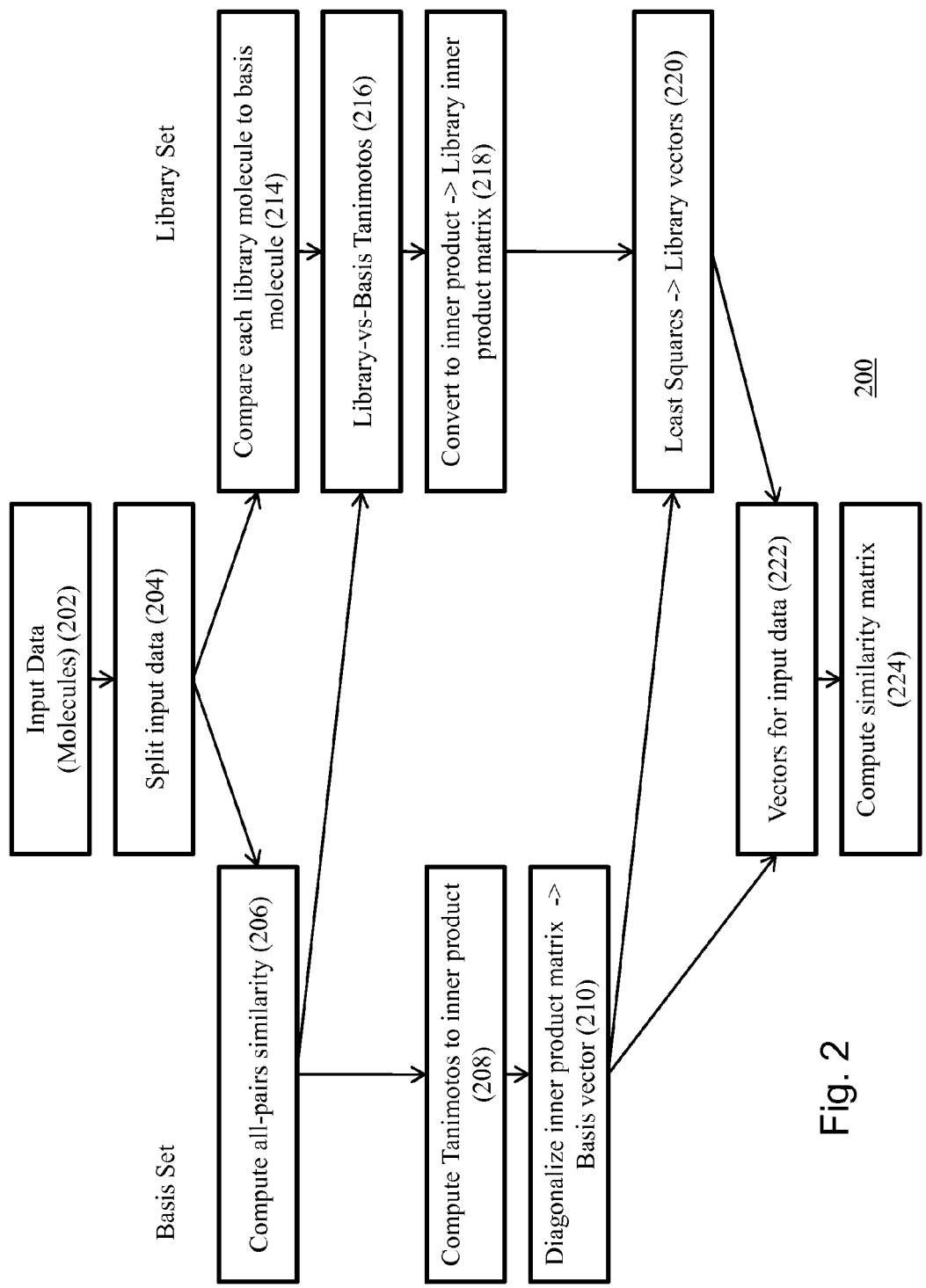
FIG. 2 is a flowchart of a method according to the present invention.

Fast Approximation of New Vectors. The above procedure for deriving molecule vectors requires computation of $O(k^2)$ molecular similarities. Given a fixed basis set of molecules, it is possible to approximate vectors for new molecules in a fixed amount of time for each new molecule by least-squares. Given a library molecule (that is, one not originally in the basis set) $L_i$ and the matrix M of basis vectors, a vector for $L_i$ can be constructed according to method 200 as shown in FIG. 2.

As shown at step 202, method 200 receives input data for a set of molecules. At step 204 the set of molecules is split into a basis set of molecules, $B_1 \ldots B_n$, and a library set of molecules, $L_1 \ldots L_k$, where n<<k. In an embodiment, step 204 is performed as a random process. In yet another embodiment, step 204 is performed by a clustering process as described herein.

At step 206, for the basis set, pair-wise similarity is computed with the source measure. The result is a Tanimoto matrix for the basis set As shown in at step 214 of FIG. 2, the method of the present invention compares similarities between $L_i$ and all basis molecules $B_j$. At step 216, method 200 receives the result of step 214 and step 206 to compute library-vs-basis Tanimotos. At step 218, the Tanimoto results of step 216 are converted to inner products to create a library Inner Product matrix. The method transforms similarities to inner products $G_{ij}$. Inner products are then stored in a vector $T = [G_{i1}, G_{i2}, \ldots, G_{ik}]^T$.

Continuing from step 206, for the basis set at step 208, method 200 converts the Tanimoto matrix of step 206 to inner products according to the relationship of Equation 2. The result is an basis Inner Product Matrix. Then according to the relationship of Equation 3, the basis Inner Product Matrix is diagonalized to create a set of basis vectors as shown in step 210.

Using the results of step 210 and step 218, method 200 solves the equation $M\vec{x} = T$ by a least squares computation at step 220 that yields a set of library vectors. The resulting vector $\vec{x}$ contains the vector that best approximates the given inner products, in a least-squares sense, and therefore is the molecule vector for molecule $L_i$. The basis vectors of step 210 and library vectors of step 220 are then converted to input data at step 222 according to the relationship of Equation 1 so as to compute the similarity matrix of step 224.

Method 200 of FIG. 2 allows the approximation of vectors for a large library of molecules in time linear in the size of the library. It is parallel once the basis set has been computed, making it a computationally attractive method for operation on large libraries.

RESULTS: The present invention was tested for effectiveness. The results of such testing are presented below.

Similarity Measures. To demonstrate the generality of the methods of the present invention, we have tested it against similarity measures of various types, as implemented in the OpenEye Scientific Software (Santa Fe, N. Mex.) oechem, oeshape, and oeet toolkits. Representing substructure-fingerprint-based methods is LINGO, a similarity measure which counts the number of substrings in common between the SMILES representations of a pair of molecules. "ROCS," a three-dimensional (3D) shape comparison method which finds the maximal volume overlap between Gaussian representations of molecule shape, represents 3D shape methods. A variation on shape-based ROCS, known as the ROCS Color Tanimoto, uses a similar volume overlap optimization on virtual "color" atoms representing chemical functionalities. We use this color ROCS to demonstrate the generalizability of the present invention to 3D methods that include distinct atom types, not all of which interact with one another. Finally, ZAP, a Poisson-Boltzmann solver which calculates and compares electrostatic fields around molecules, represents electrostatic similarity methods.

Molecules Tested. We draw molecules for testing from a diverse set of collections of drug and drug-like molecules. Most of our tests were performed on a 57,253 molecule database, hereafter named "Maybridge+BBP," constructed from the union of the Maybridge Screening Collection and a blood-brain barrier penetration data set. For Maybridge+BBP, 3D conformers were generated using OpenEye's OMEGA software. When calculating Tanimotos using ROCS, multiconformer (200 conformer maximum) fit molecules were aligned against single-conformer references, and the maximum Tanimoto over any pair of conformations for the molecule pair was used. Detailed configuration parameters passed to ROCS and OMEGA are included in the Appendix.

In the test for generalizability of the present invention, we used the 1665 molecules tested in PubChem Assay #677, an assay for novel allosteric modulators of the M1 muscarinic receptor. To test the sensitivity of the present invention against the source of molecules for the basis set, we draw basis molecules from the Maybridge+BBP set and also from the Asinex Gold Collection and the Maybridge Fragment Library, commercial libraries used for compound and fragment screening. Finally, the virtual screening test draws its molecules from the Directory of Useful Decoys, version 2, a computational drug-discovery data set specifically designed to confound methods based on common physical parameters, such as molecular weight and cLogP. For all 3D similarity measures other than the 57,253 molecule Maybridge+BBP set, molecules were assigned single conformers by Open-Eye's OMEGA software. Charges for all molecules were assigned using the AMI-BCC charge model implemented in OpenEye's oequacpac toolkit.

Differences in setup (i.e., multiconformer vs. single conformer) between data sets are due to the fact that we made use of existing databases already in use for other drug discovery projects. These differences are not significant to the content of the present disclosure. Insofar as an object of the present invention is to reproduce the results of existing similarity measures, we demonstrate comparable performance to the source similarity measure regardless of how the molecules were prepared for the source measures.

Basis Size and Dimensionality. To evaluate the present invention's ability to approximate molecular similarities on data sets of varying size, we used the present invention to approximate the ROCS shape Tanimoto for test sets of 19,000 and 50,000 molecules drawn at random from Maybridge+ BBP. This was performed multiple times over a large number of basis sizes and dimensionalities (in all cases, the 19,000 or 50,000 library molecules were disjoint from the basis molecules). Tanimotos were computed using multiconformer query molecules matched against single-conformer references; the Tanimoto of the best-matching query conformer against the reference was used as the Tanimoto for the molecule pair. Detailed settings for ROCS are provided further below. As a measure of performance, we calculated the root-mean-square (RMS) deviation between the results of the present invention and ROCS Tanimoto over all pairings of these 19,000 molecules (FIG. 3: 19,000×19,000=361 million Tanimotos) or 50,000 molecules (FIG. 4: 50,000×50,000=2500 million Tanimotos).

Figure 3:
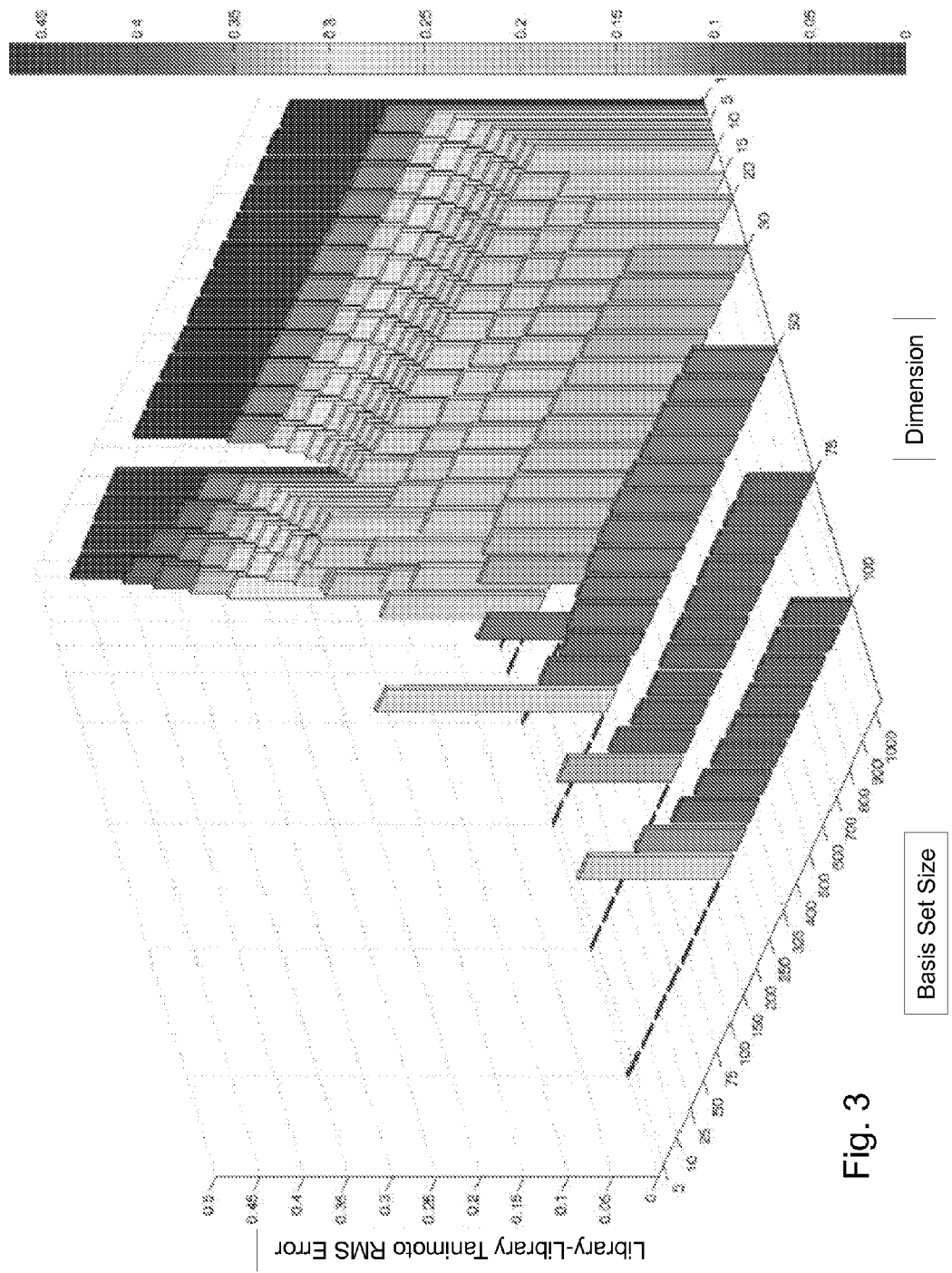
FIG. 3 is a graph showing results of the present invention.

Among other things, FIG. 3 shows the RMS Tanimoto error versus basis size and dimensionality of approximation for the method of the present invention on ROCS Shape Tanimoto. The 19,000 library molecules (361 million total Tanimotos) used to calculate root-mean-square error (RMSE). Each bar averaged over at least 10 random bases of given size.

Figure 4:
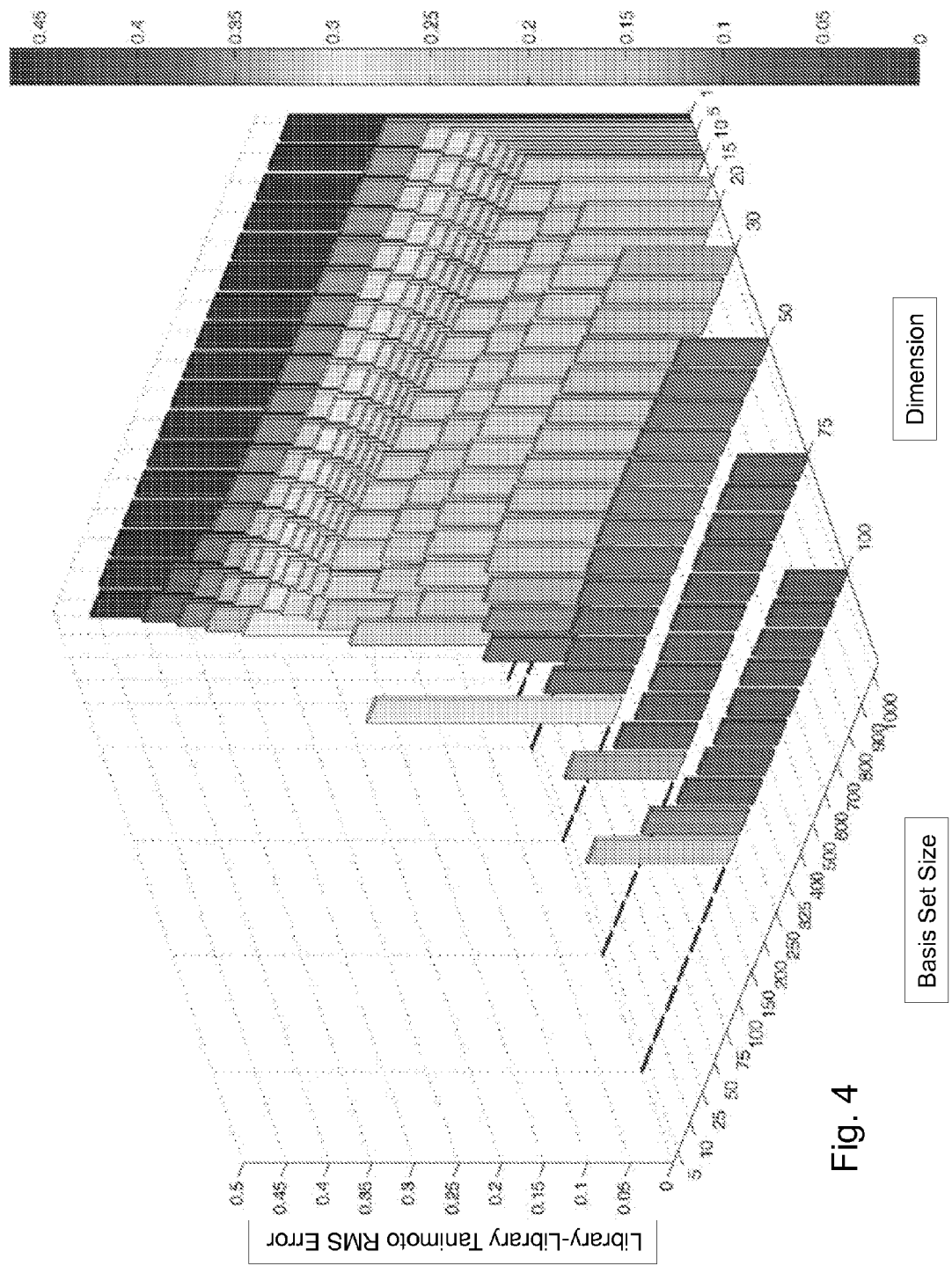
FIG. 4 is a graph showing results of the present invention.

Among other things, FIG. 4 shows the RMS Tanimoto error versus basis size and dimensionality of approximation for the method of the present invention on ROCS Shape Tanimoto. The 50,000 library molecules (2500 million total Tanimotos) used to calculate RMSE. Each bar averaged over at least 10 random bases of given size.

Two trends are evident from the data. First, the error in the present invention's approximation of the shape Tanimoto falls rapidly at first with the addition of more dimensions and then levels off around 75-100 dimensions. Most of the error falloff occurs in the first few dimensions, with gains beyond 30 dimensions coming much more slowly. A similar trend also appears for basis size; a large error is present for small basis sizes (especially in high-dimensional approximations), as a consequence of overfitting the vector model, but this falls off rapidly as the basis size increases. This result is stable even as we scale to a data set more than double the size. The test set comprising 50,000 molecules required neither more eigenvectors nor a larger basis set to achieve root-mean-square error (RMSE) comparable to that found on the 19,000 molecule test set.

Ultimately, the present invention is able to approximate the ROCS shape Tanimoto to within approximately 0.08 RMSE around 75-100 dimensions and a basis size of 500-1000, for both the 19,000 and 50,000 molecule test sets.

Figure 5:
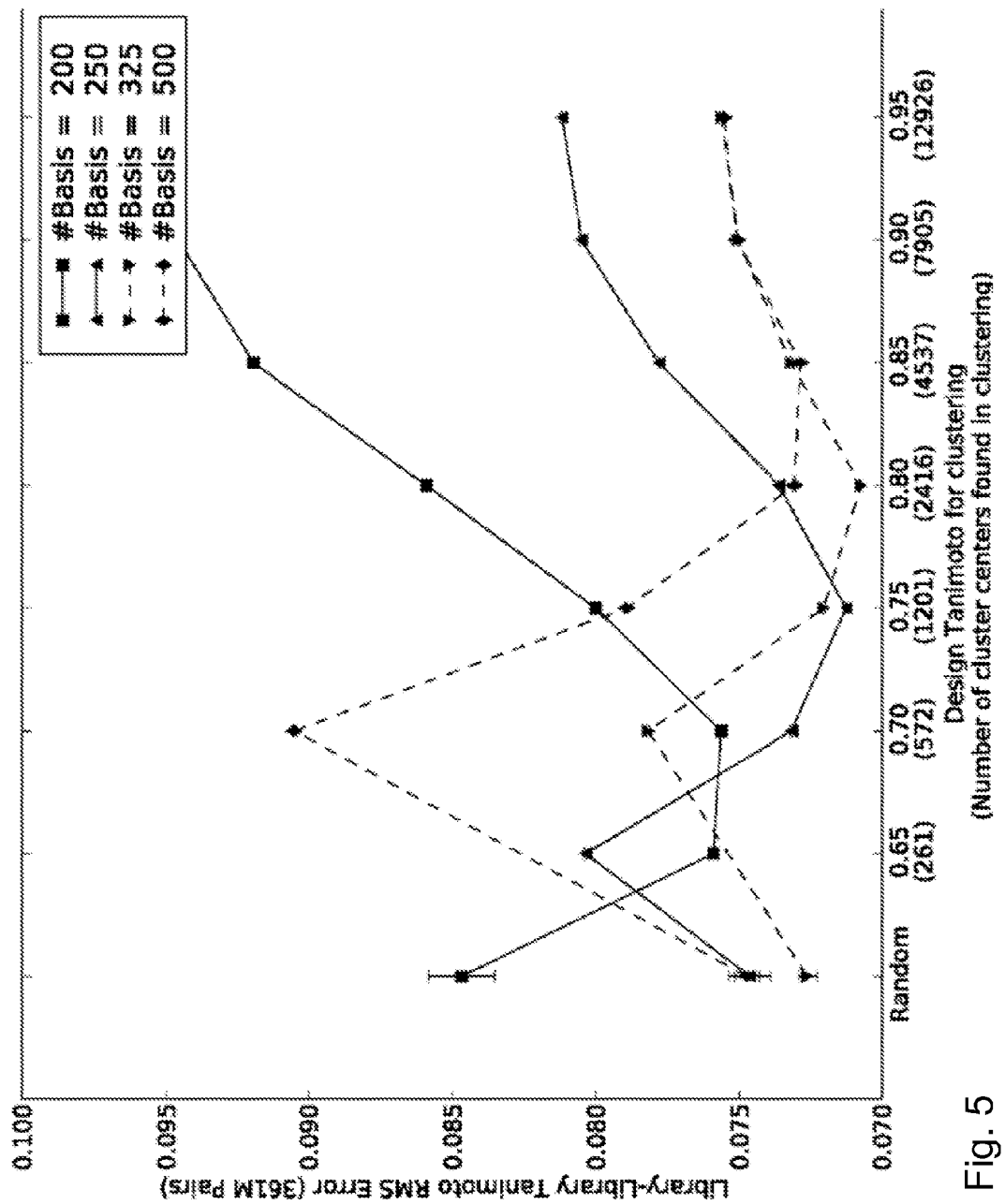
FIG. 5 is a graph showing results of the present invention.

Basis Selection Strategies. To test the sensitivity of the present invention as to how the basis set is chosen, we compared randomly chosen basis sets with basis sets chosen such that basis molecules corresponded to "representative" shapes in the data set. To choose representative molecules, we clustered the Maybridge set using the dbclus algorithm at several Tanimoto cutoff values; the cluster centers chosen were used as the representative shapes. For each measured basis size N, we ran an implementation of the present invention in 75 dimensions using a basis consisting of N randomly chosen molecules or the N cluster centers with largest number of neighbors (ties broken at random). The resulting library RMSEs are plotted in FIG. 5. RMS Tanimoto errors are plotted for approximations from the method of the present invention for ROCS shape Tanimoto constructed from randomly selected basis sets and basis sets chosen by molecule clustering. All Tanimotos evaluated over 361 million molecule pairs.

For any basis set larger than 200 molecules, it was possible to find an approximation using the present invention with lower RMS error than that resulting from the random basis; however, in all cases such error reduction was small, on the order of 0.005 Tanimoto units. Interestingly, the optimal clustering Tanimoto value differed by basis size. The optimal Tanimoto (that is, the cluster set with lowest RMSE) increased with increasing basis size, suggesting that, as more basis molecules are added, it is somewhat advantageous to select tighter clusters as basis elements.

Figure 6:
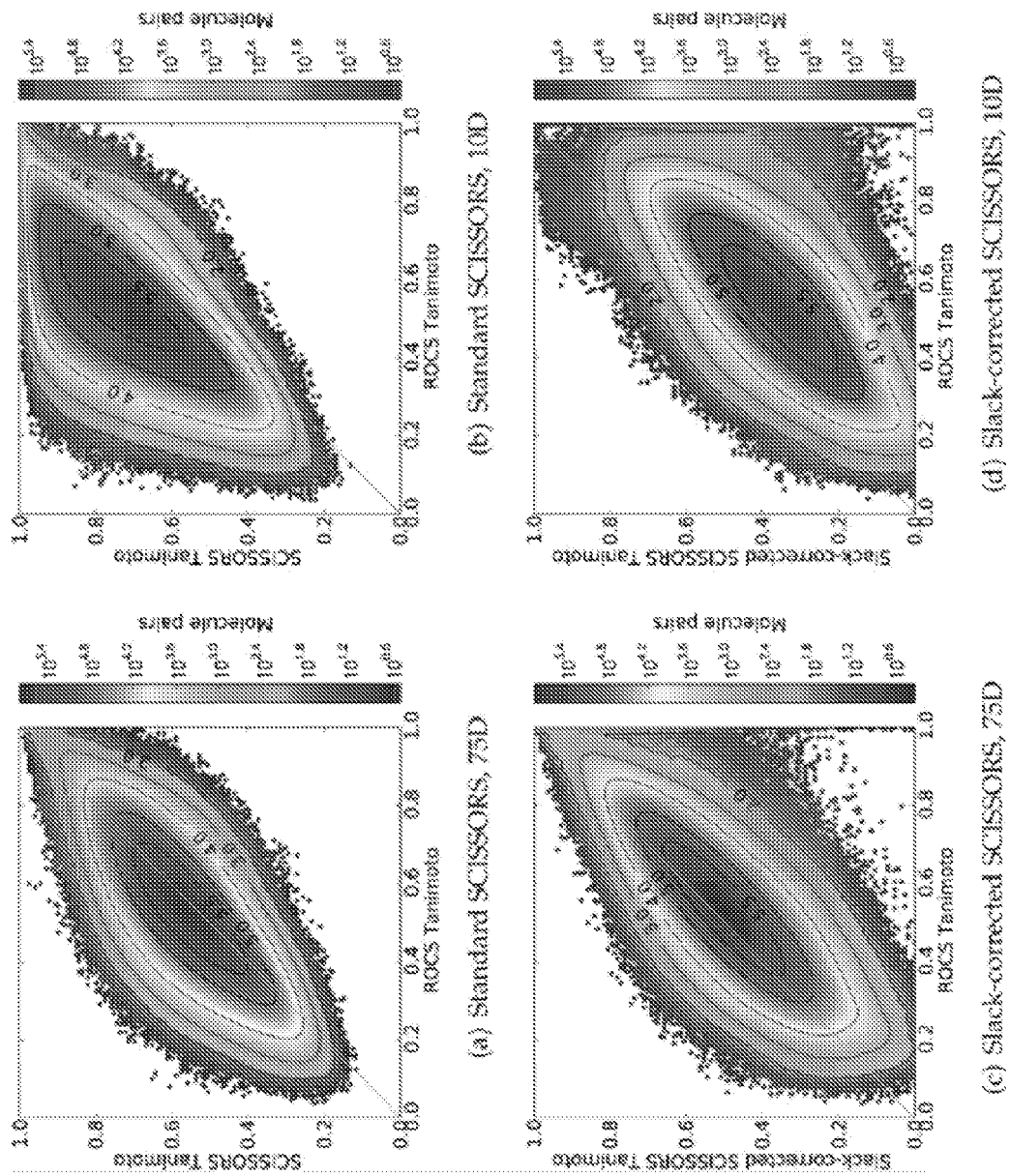
FIG. 6 includes graphs showing results of the present invention.

Corrected Tanimotos. In FIG. 6, we examine the effect of the slack coordinate correction term introduced earlier. Density plots are shown for the method of the present invention and slack-corrected method of the present invention Tanimoto approximations of ROCS Shape Tanimoto for 361 million molecule pairs from Maybridge. Contours are labeled as $\log_{10}$ of contour height. The y=x line is drawn for reference. Because the purpose of the correction term is to account for eigenspectrum density truncated in a low-dimensional approximation, we examine two cases, 10- and 75-dimensional approximations. FIG. 6 is a density plot of the method of the present invention and corrected Tanimotos versus ROCS Tanimotos using the 19,000 molecule test subset of Maybridge+BBP also used in FIG. 3. In FIG. 6, density contours that are symmetric about Y=X indicate that the plotted Tanimoto values have an unbiased error with respect to the original Tanimoto value, which aids in the preservation of rank ordering.

As expected from the earlier results, in 75 dimensions, the standard method according to the present invention, Tanimoto values are tightly clustered along the Y=X line, and the contours of the density plot continue to be aligned along this Y=X axis even out to low densities, indicating an overall preservation of rank ordering. In contrast, in 10 dimensions, the Tanimotos from the method of the present invention, as expected, almost always overestimate the true Tanimoto. Furthermore, the contours are no longer ellipses symmetric about Y=X (or a parallel line), which indicates poorer rank-ordering performance.

As expected, the slack coordinate correction leaves the high-dimensional case largely unaffected, with the major exception of a large group of errors at ROCS Tanimoto=1.0. These are caused by self-comparisons; the slack coordinate method does not respect the constraint that the Tanimoto of a vector against itself ought to be 1. However, in the low-dimensional case, the slack correction makes a significant difference. Leaving aside the known artifact at ROCS Tanimoto=1.0, the overall shape of the density contours is shifted below the diagonal but is symmetric. This indicates that, with the exception of a constant shift, the slack-corrected values are much more accurate than the uncorrected low-dimensional values.

Virtual Screening. To illustrate the utility of Tanimoto values derived from the method of the present invention in virtual screening, we used the present invention on the ROCS-shape Tanimoto to do a virtual screen on the Directory of Useful Decoys (DUD) test set. DUD is a collection of "systems" consisting of target proteins and associated small molecules. For each system, a certain number of molecules known to bind the target are designated as "ligands"; the rest of the molecules (36 times the number of ligands) are "decoys" with similar physical properties believed to not bind the target. We used a previously published protocol to evaluate performance and statistical significance; for clarity, we summarize the protocol below.

For each protein system in DUD, we used ROCS and the method of the present invention (with three different basis sets) to calculate the Tanimoto of every ligand molecule against every other molecule in the system. For each ligand molecule, we ranked all other molecules in order of decreasing Tanimoto similarity, modeling a screening experiment in which given one active compound, one wishes to find other actives in a pool of inactive molecules. All molecules used were single conformer; settings for ROCS are given further below. All Tanimoto values from the method of the present invention were computed in 10 dimensions as uncorrected Tanimotos from the method of the present invention. Basis sets were drawn from the Maybridge Screening Collection, the Asinex Screening Collection, and the Maybridge Fragment Library to illustrate the effects of different basis choices on performance.

Figure 7:
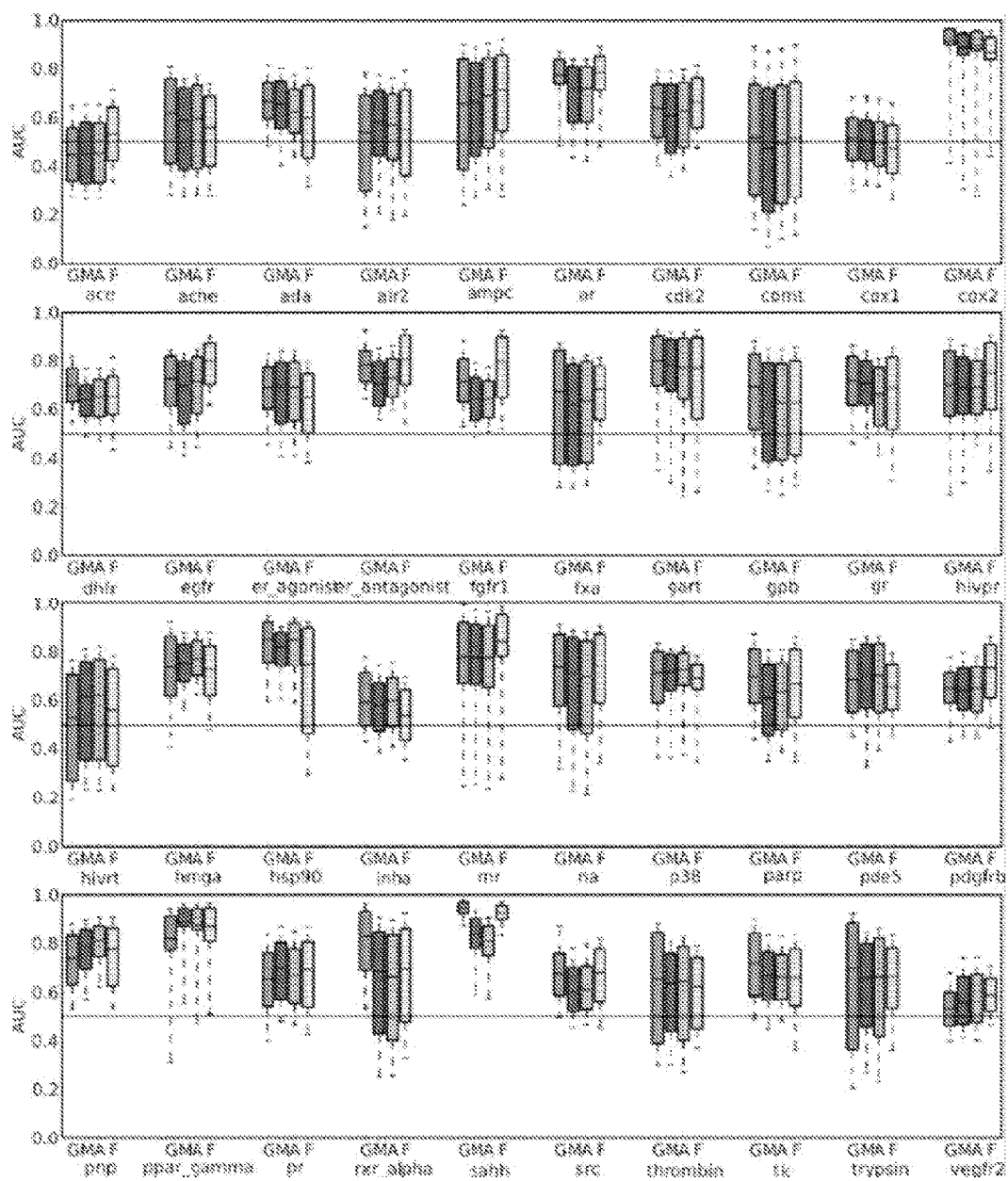
FIG. 7 includes graphs showing results of the present invention.

The ROC area under curve (AUC) for this ranking was calculated according to the method in Clark (Clark, R. D.; Webster-Clark, D. J., "Managing bias in ROC curves," *J. Comput.-Aided Mol. Des.*, 2008, 22, 141-146.). Ligand molecules were considered true positives; false positives were any decoys ranked higher than a true ligand. A bootstrapping procedure was used to estimate the 68 and 95% confidence intervals on the calculated AUC values. These AUCs and confidence intervals are illustrated in FIG. 7. As shown, ROC AUC values on each system of the DUD test set are plotted. Reported are the mean AUC averaged over each ligand in the system (line), the 68% confidence interval on the AUC (box), and the 95% confidence interval on the AUC (whiskers). Within each system, results are reported for ROCS (G) and the method of the present invention using basis sets from the Maybridge Screening Collection (M), the Asinex Screening Collection (A), and the Maybridge Fragment Library (F). All approximations from the method of the present invention were done in 10 dimensions; Maybridge and Asinex sets used a 500 molecule basis set; and the Maybridge Fragment set was 473 molecules, the size of the entire library.

For almost all systems, the performance of the different basis sets for the method of the present invention are statistically indistinguishable from each other and from that of the original ROCS Tanimoto. In particular, the Maybridge and Asinex basis sets, which are drawn from different libraries but which likely have overall similar characteristics (as both are screening libraries) perform almost identically. The Maybridge Fragment basis is an outlier on several systems; it is likely that this is because these molecules are significantly smaller (in volume/mass) than the drug-like molecules in DUD, indicating that at least rudimentary physical property matching is a prudent step in the use of the present invention. It is interesting, however, that there were so few outliers using the fragment basis set, as similarity measures often fail when comparing fragments to elaborated molecules; we have not explored the reasons for this performance in detail.

Similarity Measure Generalizability. To assess the generalizability of the present invention to chemical similarity measures other than the ROCS shape Tanimoto, we evaluated the performance of the present invention on four similarity measures: ROCS shape and color, LINGO, and ZAP's ET, or electrostatic, Tanimoto. All Tanimotos were originally evaluated on a collection of 1665 small molecules from a screen for allosteric modulators of the M1 muscarinic receptor; for the present invention, both basis and library molecules were drawn from this same pool. All tests were conducted with 1000 library molecules, with RMSE evaluated over an all-pairs (1000×1000=1 million Tanimotos) similarity comparison. For the electrostatic Tanimoto, molecules were first overlaid using ROCS before electrostatic field calculations.

Figure 8:
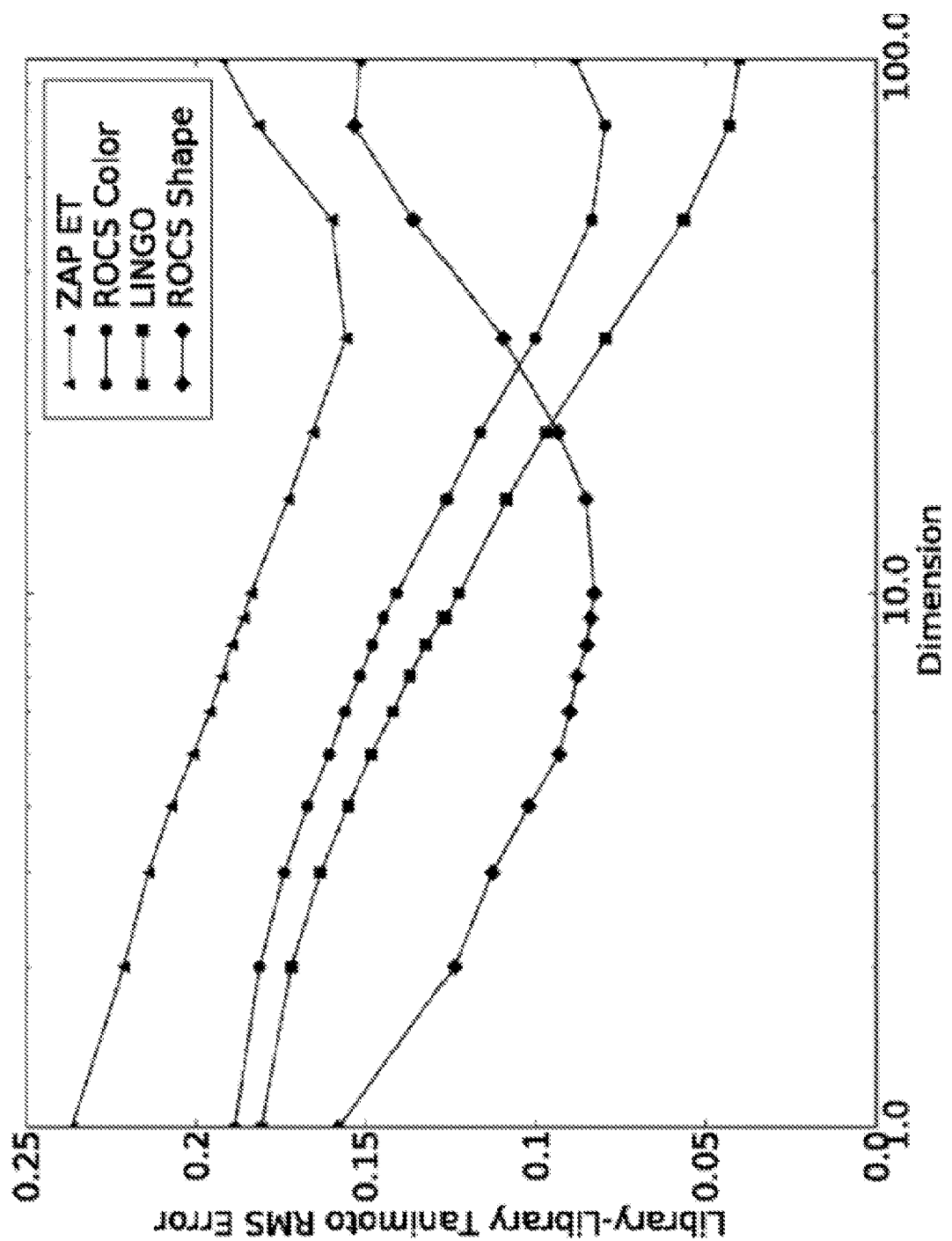
FIG. 8 is a graph showing results of the present invention.

FIG. 8 plots the Tanimoto RMSE for the present invention for each similarity measure in the large basis (600 molecules) limit as a function of dimensionality. Three trends are particularly notable. RMS Tanimoto error is plotted from approximations from the present invention to several molecular similarity measures, as a function of dimensionality of approximation. All tests were conducted with a basis size of 600 molecules and a test set size of 1000 molecules. First, on this data set, all the similarity measures show nonmonotonic error behavior as the number of dimensions increases, most likely reflecting eventual overfitting (an insufficient number of basis molecules for further dimensions). Second, the present invention generalizes well to approximating both the ROCS color and the LINGO Tanimotos, with RMSEs under 0.1 in both cases. Finally, ZAP's electrostatic Tanimoto appears to be inapproximable by the method of the present invention.

Figure 9:
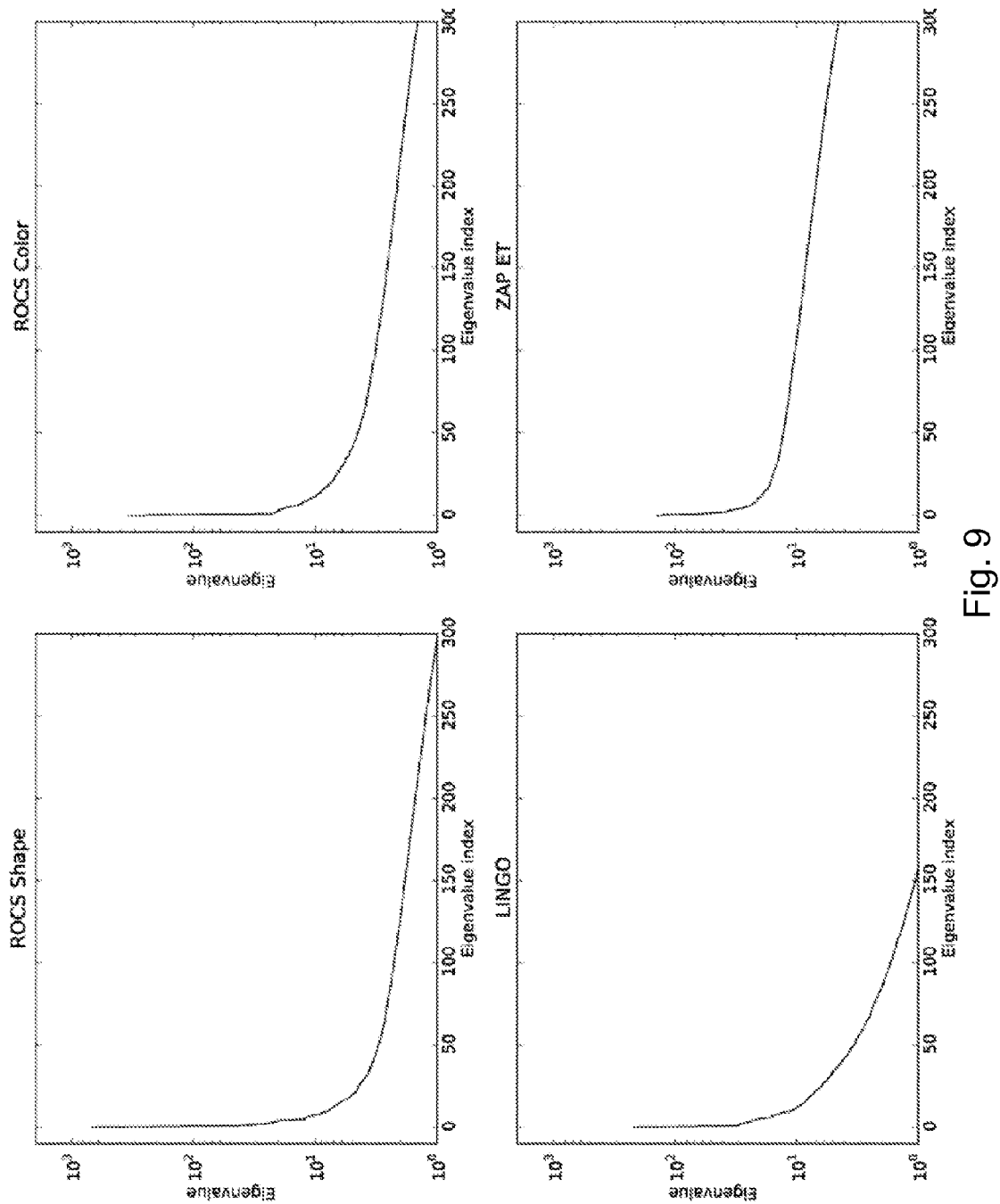
FIG. 9 includes graphs showing results of the present invention.

FIG. 9 explores why only certain measures are approximable by the method of the present invention. The eigenvalue spectra for Gram matrices resulting from four similarity measures on 1000 molecules from the MI muscarinic data set is plotted. Each subplot plots the value of the top 300 eigenvalues from a basis set of size 1000 computed for each of the four similarity measures, on a log scale. For all three well-approximated measures, the magnitude of the 100th eigenvalue has fallen off more than 2 log units relative to the first (largest) one, indicating that high dimensions rapidly become less important to the approximation. In contrast, the ET Tanimotos eigenspectrum falls off much more slowly; even after 300 dimensions, it has not fallen 2 log units. It is this characteristic of the eigenspectrum (insufficiently rapid falloff) that makes a low-dimensional linear approximation to the ET Tanimoto impossible.

Tanimoto Computation Speed. The precalculation step of method of the present invention is extremely efficient compared to the evaluation of the source similarity measure. We benchmarked the precalculation step for calculating molecule vectors on a 20,480 molecule subset of Maybridge+BBP, using a 500 molecule basis set drawn from the same database. Timings for each phase of precalculation of the present invention on one core of a 3 GHz Intel Xeon-based (Core 2 architecture) Mac Pro are presented in Table 1 (further machine details are presented further below). The precalculation time is dominated by ROCS calculations; the spectral decomposition and least-squares inference for method of the present invention take less than 5 seconds, compared to nearly 11000 seconds for the basis versus basis and library versus basis ROCS computations.

A significant benefit of the present invention is that it calculates accurate estimates of molecular similarity extremely rapidly once library vectors have been inferred. This is particularly true in the case of the ROCS shape and color similarities, which are industrially important but expensive to calculate. We measured the OpenEye ROCS implementation's performance at approximately 1000 comparisons/s per core on a 3 GHz Mac Pro, while performing the basis-basis and library-basis ROCS comparisons for the above benchmark. In contrast, our C code to evaluate Tanimotos from the present invention (compiled with gcc 4.0.1 and GotoBLAS2) is capable of computing approximately 50 million similarities/s (in 64 dimensions) on one core of the same CPU. With precomputed library vectors, then, the present invention is around 50,000 times faster than a direct calculation of Gaussian overlap.

Indeed, the method of the present invention is fast enough that for large similarity matrix problems, it can be faster to recalculate similarities on-the-fly from vectors of the present invention than to precalculate all similarities and read them back from disk. This leads to a significant savings in storage, as the storage required for the molecule vectors scales as $O(N)$, while storage for a similarity matrix scales as $O(N^2)$. The combination of high computation speed and reduced storage makes similarity calculations (for large scale virtual screening and data analysis) computationally feasible for data sets with N on the order of $10^5$ to $10^7$. The present invention does not solve other issues involved with large data sets (e.g., file handling and molecule preparation), it is able to reduce both computational and total data storage burdens for large-scale problems. In terms of CPU time alone, it can make difficult problems fast and intractable problems tractable.

Connections to Previous Work. Previous Methods to Characterize Chemical Space. Several methods have been applied in past work to characterize chemical space by learning relevant dimensions along which chemicals vary to find vector embeddings of molecules. In this section we discuss past work which has used multidimensional scaling and other similar techniques to find vector embeddings of molecules based on particular similarity representations.

Multidimensional scaling has previously been applied to chemical data sets in order to reduce the dimensionality of binary molecular fingerprints. This approach has been used for combinatorial library design; by computing coordinates for each molecule and treating each dimension as a property, it is possible to maximize the distance among molecules to select a maximally diverse library. However, using MDS directly in this manner is not scalable to large compound sets, as it requires a full $N^2$ similarity matrix.

There have also been prior efforts to develop scalable versions of MDS-based methods. One method, due to Nicholls (Nicholls, A.; Grant, J. A, "Molecular shape and electrostatics in the encoding of relevant chemical information," *J. Comput.-Aided Mol. Des.*, 2005, 19, 661-686), focuses on similarity metrics; that is, on similarity measures that compute a distance between pairs of molecules, such that these distances obey the triangle inequality. The Nicholls method, after computing coordinates for a basis set of molecules using MDS, computes coordinates for a new nonbasis molecule by triangulation based on distances to each of the basis molecules.

The principal difference between the method of the present invention and these older MDS-based methods is use of least-squares approximation to calculate coordinates for nonbasis molecules in the present invention. Least squares allows the present invention to scale well to large data sets, unlike the original methods using MDS for dimensionality reduction. Furthermore, because we approximate inner products rather than distances and use least-squares rather than triangulation to calculate coordinates, we do not assume that the approximated similarity measures are true metrics. In particular, the use of least-squares allows the present invention to calculate approximate coordinates even in the nonmetric source similarity case (in which the triangulation equations would have no consistent solution). The similarity of the present invention is a metric (or pseudometric, in the case of the slack-corrected Tanimoto) approximation to the source measure.

Raghavendra and Maggiora (Raghavendra, A. S.; Maggiora, G. M., "Molecular Basis Sets —A General Similarity-Based Approach for Representing Chemical Spaces," *J. Chem. Inf. Model,* 2007, 47, 1328-1340) developed a symmetric—orthogonalization method to calculate vector embeddings of molecules in an arbitrary similarity space. The Raghavendra and Maggiora (RM) method calculates a pairwise similarity matrix on a small set of basis molecules, using this to find vectors for the basis, and then projects library molecule vectors onto this space by transforming library-basis similarity values. It is presented only as a method to describe chemical space and not as a method to approximate similarities. Several mathematical limitations impact the applicability of this method for both purposes.

One critical difference is in the treatment of the basis similarity matrix, the entries of which are Tanimotos. The RM method treats these entries as though they were inner products; however, as equation 1 shows, the Tanimoto is a function of an inner product but not an inner product itself. This inaccuracy will distort vector spaces inferred by the method.

TABLE 1

Precalculation Step Timings for 20,480 Library Molecules using the present invention

| step | time (sec) |
|---|---|
| basis matrix ROCS calculation | 262 |
| basis vector calculation (eigendecomposition) | 0.33 |
| library vs basis ROCS calculation | 10 732 |
| library vector calculation (least-squares) | 4 |

[a] Using a 500 molecule basis set and one core of a 3 GHz Intel Xeon-based Mac Pro.

Furthermore, this method is unable to handle molecular similarities which do not result in positive definite Gram matrices (i.e., non-Euclidean measures). The method of the present invention handles these in two ways. First, the use of the slack correction allows approximation of dimensions associated with the negative eigenvalues in a nonpositive definite similarity measure. Second, a typical use of the present invention will retain fewer eigenvalues/eigenvectors (dimensions) than can be computed from the matrix. This allows a positive definite approximation of nonpositive definite measures. It also improves the statistical reliability of our vector approximations. The RM method projects library molecules onto the full number of dimensions computed from the basis matrix (i.e., number of dimensions=number of basis molecules). However, as shown in FIGS. 3 and 4, fitting to a number of dimensions similar to the number of molecules leads to large approximation errors from overfitting. Thus, the method of the present invention is more faithful to the mathematics behind similarity coefficients, is more flexible by allowing approximation of non-Euclidean measures, and is more accurate because it adds the ability to avoid overfitting.

Connections to Kernel PCA. Kernel principal components analysis (kernel PCA) is a nonlinear variant of PCA that, given data in an input vector space, finds the principal components of the data in a different vector space known as the feature space. The dimensionality of this feature space is often very high (possibly infinite). The computation is achieved by the use of kernel functions, which map a pair of points in the input space to a real number that is interpretable as the inner product of the two points in the feature space, without requiring an explicit expansion of the points into the feature space.

Above, we derived the algorithm for the present invention from classical multidimensional scaling. The method used in the present invention to derive basis vectors is related to kernel PCA (which is itself linked to multidimensional scaling). In particular, by transforming chemical similarity Tanimoto values to inner products, we treat transformed chemical similarity functions as kernels that map molecules from a hypothetical "molecule space" into a feature space induced by the particular similarity function. Because the mathematical methods underlying the present invention are similar to those of kernel PCA, several optimality properties of kernel PCA carry over to the present invention. As was previously argued using the derivation from multidimensional scaling, an expansion of a molecule in k dimensions of a chemical feature space has a minimum mean-squared approximation error, compared to any other choice of k directions (e.g., as might be derived from a truncation of a Cholesky decomposition).

Furthermore, the k directions calculated from kernel PCA have minimal representation entropy. As a consequence, no other orthogonal basis transformation can reproduce the given inner product matrix with the same accuracy in fewer bits. This property provides a rigorous bound on the accuracy of vectors calculated by the present invention; no other method evaluating chemical similarity inner products by dot products between real vectors can achieve a better coverage of the variance in the training (basis) matrix with fewer bits than used by the present invention.

There are several key differences between the present invention and kernel PCA related to the treatment of the Gram matrix. First, following multidimensional scaling, we do not rescale the eigenvectors obtained in the diagonalization of the Gram matrix. Additionally, most commonly used chemical similarity measures, when transformed from Tanimotos to inner products, do not induce the type of kernel usually used with a kernel PCA approach (known as a Mercer kernel), as their Gram matrices usually have negative eigenvalues. More importantly, prior to diagonalizing the Gram matrix, we do not center the data to have zero mean. As a consequence, the first eigenvector reflects the mean value in the feature space. As will be shown in the next section, this is key to partial interpretability of coordinates derived from the method of the present invention.

Interpretation of Chemical Similarities. Besides its use in constructing vector approximations, the inference procedure of the present invention also gives insight into the nature of the chemical space induced by a given similarity measure. In particular, for well-approximated measures for which a molecule-molecule inner product can be defined, we can interpret the meaning of the first vector coordinate and gain an understanding of the measure. Our example here is the Gaussian volume overlap measure used by ROCS.

ROCS defines its "shape Tanimoto" as Equation 7, in which $O_{xy}$ represents the value of the overlap volume between molecules x and y, which have been rotated and translated to maximize their volume overlap.

$$T_{AB} = \frac{O_{AB}}{O_{AA} + O_{BB} - O_{AB}} \quad (7)$$

This equation has clear similarity to the conventional vector Tanimoto (equation 1); by analogy, for ROCS, we can treat the maximum overlap volume between a pair of molecules as the inner product between these two molecules. Recall that for a similarity measure to be well-approximated by the method of the present invention, we require that the eigenvalue spectrum of the similarity measure falls off sufficiently rapidly, such that each successive dimension is significantly less important than the one preceding it.

Consider such a measure on molecules A and B and their vector approximations $\tilde{A}=[a_0, \ldots, a_n]$ and $\tilde{B}=[b_0, \ldots, b_n]$. Because the present invention is able to approximate the measure well, it is true that $\langle A, B \rangle \approx \langle \tilde{A}, \tilde{B} \rangle$. The assumption that the measure is approximated well implies (by the discussion in section on generalizability) that the eigenvalue spectrum falls off rapidly. This in turns means that the first coordinate will be the dominant component of the inner product (since further coordinates are decreasingly important), or formally, that $\langle A, B \rangle \approx \langle \tilde{A}, \tilde{B} \rangle \approx a_0 b_0$. In the special case in which A=B (the self-similarity of molecule A), $\langle A, A \rangle \approx a_0^2$.

Figure 10:
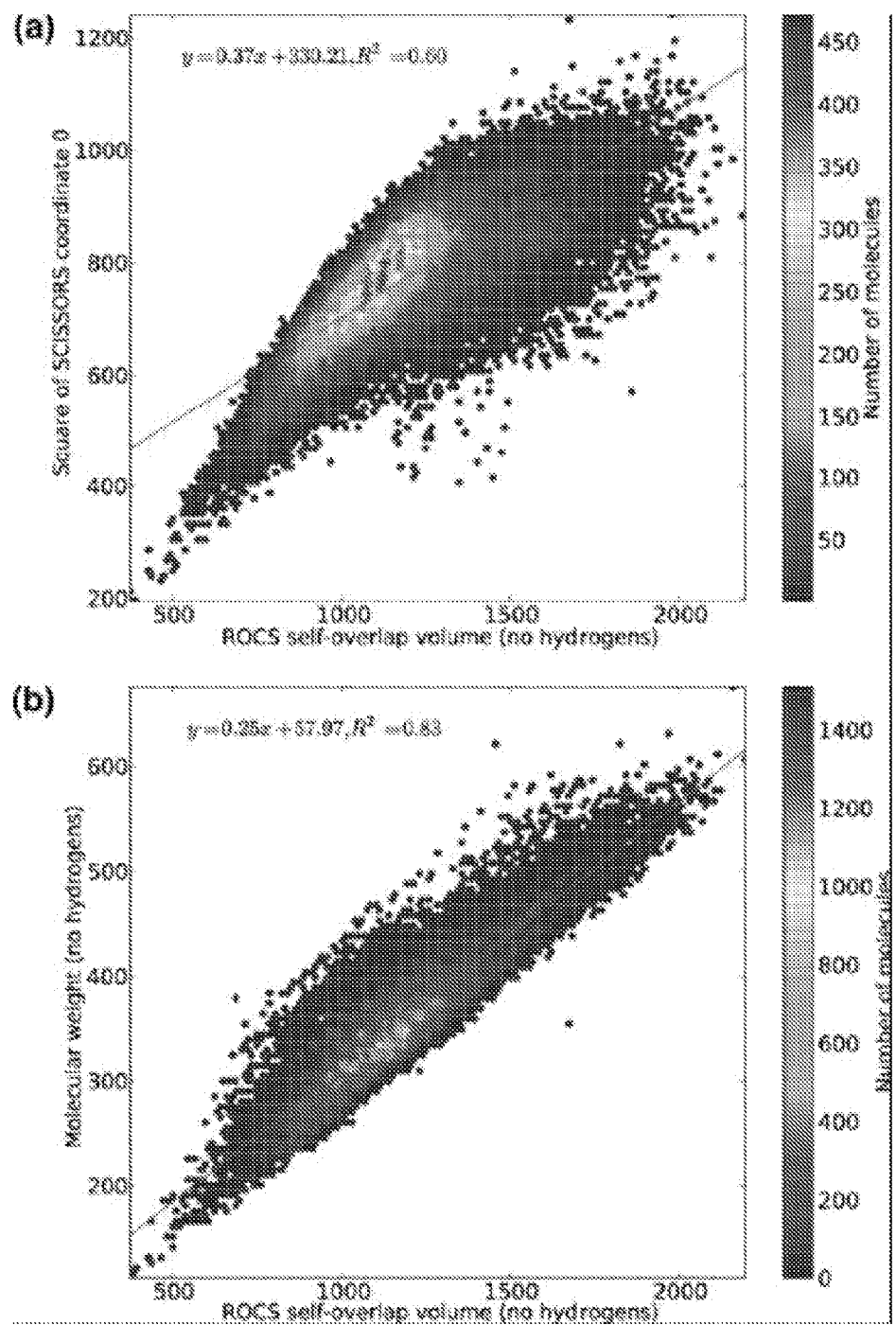
FIG. 10 includes graphs showing results of the present invention.

For the ROCS similarity measure, this implies that the first coordinate of the vector for a given molecule, and therefore the first principal coordinate of the shape space induced by the measure, is approximately equal to the square root of the molecular volume. This is illustrated in FIG. 10a, which plots the first coordinate of many molecule vectors inferred by the present invention on the ROCS shape overlap quantity against their molecular volumes. All data from 128,371 Tanimotos is computed on a DUD test set and 500 random molecules from Maybridge are used as basis. The lines show that the data are well-fit by a square-root function multiplied by a constant that represents the relative importance of molecular volume to the whole similarity measure. This demonstrates that shape-based virtual screening is largely controlled by differences in molecular volume, which correlates very closely with molecular weight (FIG. 10b).

As explained by analogy to kernel PCA, this first coordinate (which for ROCS is approximately equal to the square root of the molecular volume) reflects the mean location of the molecules in the feature space learned from the similarity measure. We do not know whether a similar chemically interpretable understanding of the second and later eigenvectors (projections onto which are the molecular coordinates) exists. It has been demonstrated that the eigenvectors calculated by kernel PCA converge, in the large-basis limit, to eigenfunctions of a linear operator on the underlying kernel. These in a sense reflect a functional basis for the kernel (or similarity measure). In general, coordinates in a kernel feature space as calculated by kernel PCA are not required to have pre-images in the input space.

Insights into Chemical Space. An interesting result of the analysis of the present invention is that relatively few basis molecules (on the order of 500-1000) were sufficient to achieve accurate estimation of shape Tanimotos for compounds in Maybridge and DUD and that the source of these molecules (Maybridge, Asinex, or Maybridge Fragment) made little difference for virtual screening. This finding is paralleled by previous results. Haigh et al. demonstrated that a reference shape set of 3119 molecules was sufficient in their "shape fingerprints" approach to reproduce shape Tanimotos and that these reference shapes were transferable across databases. Fontaine et al. found that a database of 2458 reference shapes was sufficient to cover the shape space of a one million compound single-conformer data set in their "alignment recycling" approach. Thus, our results corroborate past data showing that, although chemical space is very large, the shape space of relevant drug-like molecules may be fairly small, with only a few hundred to a few thousand basis shapes providing adequate coverage of the shape space.

Applications: Fast Library Screening and Clustering with the Method of the Present Invention. The combination of learning vectors on a small basis set with fitting of new vectors in linear time using least-squares makes possible highly accelerated library screening. A target scenario for such an application involves screening based on a similarity measure that is expensive to calculate relative to the calculation of a low-dimensional (order of 10 to 100) dot product.

Figure 11:
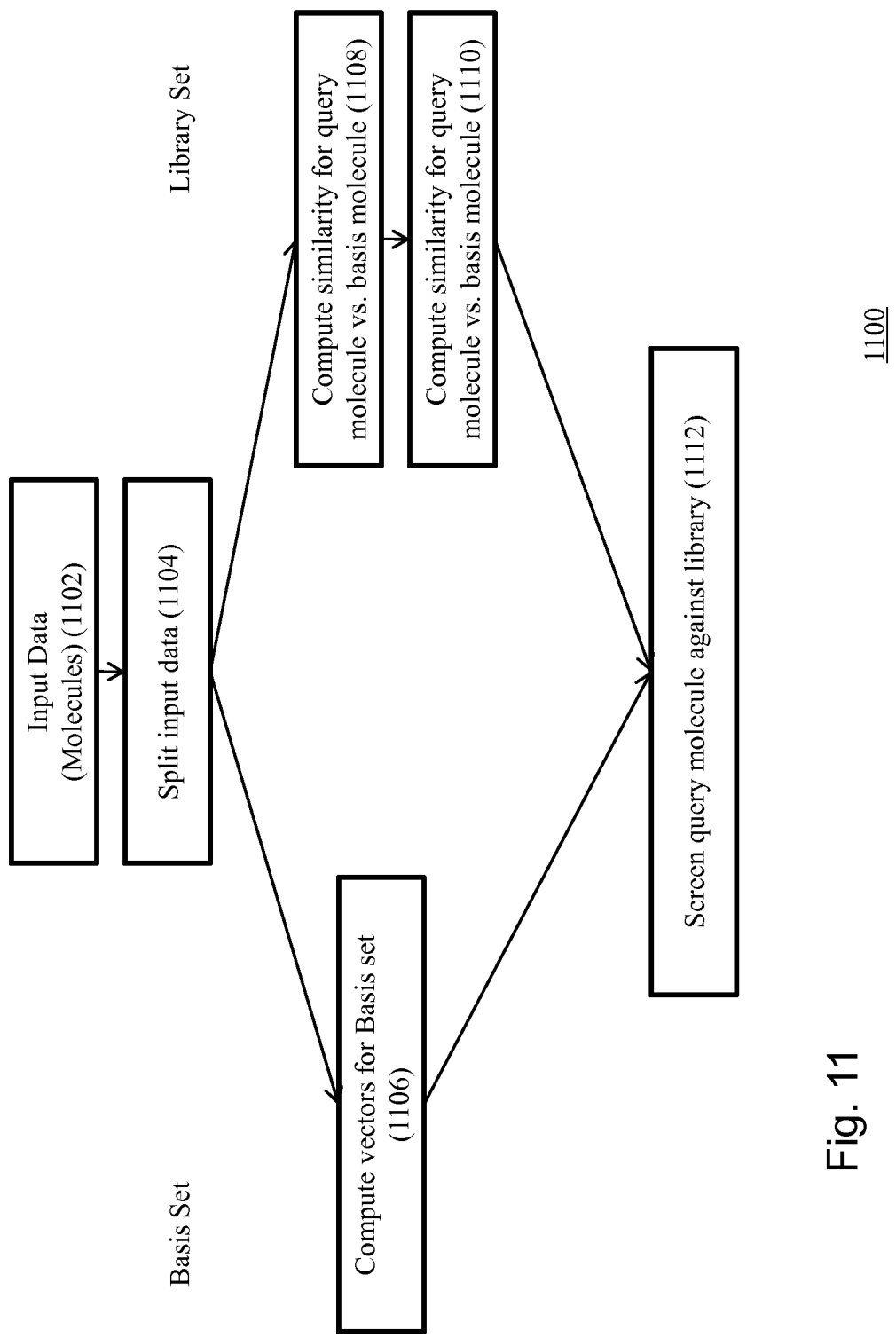
FIG. 11 is a flowchart of a method according to the present invention.

The accelerated screening protocol of the present invention follows the steps of method 1100 as shown in FIG. 11. At step 1102, molecular data is input. At step 1104, the input data is split into a basis set and a library set where the library set is much larger than the basis set. In an embodiment at step 1104, 500-1000 molecules are selected at random to serve as a basis set for the larger library. The invention, however, is not limited to these choices in the number of molecules and other particular selections. At step 1106, vectors for the basis set are computed according to the teachings described herein. In an embodiment, step 1106 is performed by eigenvalues decomposition. At step 1108, a similarity is computed for the query molecule versus the basis molecule. In an embodiment, this computation is performed for each similarity search against the library to learn the vector.

At step 1110, vectors for the library set are computed according to the teachings described herein. In an embodiment, the library set computed in step 1110 is performed by a least squares algorithm.

At step 1112, the present invention then allows for the quick screening of the query molecule against the full library. Prior to development of the present invention, such a full library search would have been computationally intractable.

The advantage to the protocol of the present invention is that, after vectors have been inferred for a given library of molecules, each new screen only requires that the source similarity measure be run against the basis set, not the whole library. The majority of the comparisons can be done using the Tanimotos from the present invention, which are thousands of times faster to evaluate.

In particular, clustering and other approaches that require the computation of a full $O(N^2)$ similarity matrix can be dramatically accelerated by the present invention. Assuming a library of size N and a basis set of size k (k, N), using method of the present invention to compute the Tanimoto similarities for the matrix requires only $O(kN)$ evaluations of the slow similarity measure, rather than $O(N^2)$. Since k can be chosen as a fixed constant, the method of the present invention is asymptotically faster in slow similarity evaluations than a straightforward similarity construction by a factor of N/k, potentially many thousands of times. This, combined with the asymptotic reduction in storage space required to quickly retrieve a similarity matrix, demonstrates that the present invention enables huge reductions in computational cost for large-scale chemical matrix problems.

The heavy computational burden imposed by popular chemical similarity measures, combined with the growing size of chemical databases, necessitates faster techniques for similarity comparison to enable large-scale cheminformatics analyses. We have described a method for rapid estimation of chemical similarities that is applicable to several popular similarity measures, including ones based on substructure comparison (LINGO) and three-dimensional shape and chemical complementarity. The present invention is able to achieve high accuracy with an efficient precalculation procedure and a relatively small molecular basis set. Given precalculated molecular vectors, the method achieves several thousand-fold speedup relative to running the source similarity metric for ROCS. We have further described a method that allows construction of a molecular similarity matrix (an important intermediate step in several algorithms) with only a linear number of evaluations of the source similarity measure, rather than the quadratic number normally required.

The algorithm of the present invention enables cheminformatics calculations to be performed with asymptotically lower costs, both in terms of computation (number of slow similarity evaluations) and storage (keeping molecule vectors on disk rather than full similarity matrices). As a consequence, the present invention will allow a new class of extreme-scale cheminformatics applications combining very large data sets with similarity measures formerly considered inaccessible for large-compound collections.

To be described now are certain details for the testing and development of the present invention.

Molecular Databases and Preprocessing. The following databases were used:

Maybridge+BBP: 56,841 of 56,842 molecules from Maybridge Screening Collection (cromoglicic acid caused Omega to crash and was excluded)+417 molecules from a blood-brain barrier penetration data set. Molecules from Maybridge were provided as 2D SDF files; BBP molecules were provided as SMILES.

Directory of Useful Decoys, release 2: 128,371 molecules provided as 3D MOL2 files with embedded charges.

Asinex Gold Collection: 233,795 molecules provided in 2D SDF format.

Maybridge Fragment Library: 473 molecules provided in 3D MOL2 format with embedded charges.

PubChem Assay #677 (discovery of novel allosteric modulators of the M1 muscarinic receptor: antagonist confirmation screen): 1665 molecules provided in 2D SDF format.

For standardization, all molecules (even if provided with 3D geometry and charge information) were converted to 2D uncharged OEBinary format using the OpenEye OEChem toolkit and then processed through the same pipeline. Molecules consisting of multiple disconnected chains (e.g., acids with counterions) were reduced to a single chemical chain using the function "OETheFunctionFormerlyKnownAsStripSalts" to keep only the largest single chain. Molecules containing atoms other H, C, N, O, F, Si, P, S, Cl, Br, and I were excluded, as these are the only atoms allowed in the MMFF94s force field used by OMEGA. Protonation, tautomer, and stereochemical state (other than invertible nitrogens) were maintained as given in the input data.

From the 2D representation, the OpenEye Omega toolkit was used to build one 3D conformer, using all default settings except for MaxConfGen=50 and MaxConfs =1. This representative conformer was used to assign charges, using the AM1-BCC charge model in the OpenEye OEProton toolkit. Final 3D conformers were then built using Omega with the following parameters:

Bondi van der Waals radii
fromCT=False
EnumNitrogen=True
EnumRing=True
BuildForceField=SearchForceField=mmff94s_Trunc
EnergyRange="5.0, 10.0, 15.0, 20.0, 25.0"
MaxConfGen=3000
MaxConfRange=50, 100, 200 (multiconformer molecules only)
MaxConfs=1 (single-conformer molecules only)
RangeIncrement=3
RMSRange="0.5, 0.75, 1.0, 1.5"

For the Maybridge+BBP data set, both multi-and single-conformer molecules were built; for all others, only single-conformer representations were used. These data sets were already in use for other ongoing drug discovery projects and thus were not rebuilt for this study. All molecule files used as input to ROCS, LINGO, ZAP, and the training routines for the method of the present invention were stored as 3D OEBinary files.

Software Versions. The Maybridge+BBP data set was prepared using OEChem 1.5.1 for file parsing, OEOmega 2.2.1 for conformer generation, and OEProton 1.2.1 for charge assignment. All other data sets were prepared using OEChem 1.6.1, OEOmega 2.3.0, and OEQuacPac (the renamed OEProton) 1.3.1.

ROCS shape and color similarities were calculated by the OpenEye OEShape toolkit, version 1.7.0. LINGO similarities were calculated using OEChem 1.6.1. ZAP ET similarities were calculated using OEZap 2.1.0.

Benchmarking of similarities of the present invention was done using an implementation written in Python and C, using Python 2.5.2, Numpy 1.1.0, and GotoBLAS2 1.13. Most calculations were performed using an older implementation of the present invention written in pure Python and Numpy; performance benchmarking was done using a newer implementation of Tanimotos using the present invention written in C using GotoBLAS2. C code was compiled using gcc 4.0.1.

Software Settings for Similarity Calculations. ROCS shape and color similarities for all accuracy tests, except the virtual screening test, were calculated using the Analytic overlap method, the Implicit Mills-Dean color forcefield, with color optimization enabled, ignoring hydrogens and using exact atomic radii (rather than coercing all radii to the carbon radius). For each pair of molecules, the best overlay was chosen from the set of all conformer pairs (for multiconformer matches) and the ROCS starting positions by selecting the overlay with the highest Combo score. The shape and color Tanimoto values from this overlay were used as the representative Tanimoto values for that particular pair.

For virtual screening, ROCS was run on the DUD molecules with the Grid overlap method, ignoring hydrogens, and with no color force field (as only the shape Tanimoto was being approximated).

For the performance benchmark (in which we measured the time to construct a representation of a 20,480 molecule library using the present invention), ROCS/OEShape was run in Analytic overlap mode with no color force field (shape only) and with default settings otherwise.

LINGO similarities were calculated using the OELingoSim module in OEChem. Aromaticity (using OpenEye aromaticity model) and chirality were perceived on molecules from their 3D structures; LINGO similarities were then calculated based on an isomeric canonical SMILES representation.

ZAP electrostatic Tanimotos were calculated using the OEET module in OEZap. Molecules were first overlaid into their optimal overlaid pose using ROCS, using the same settings as for shape/color similarity. OEET's default settings for Tanimoto similarity were used to calculate the electrostatic similarity, based on the AMI-BCC charges calculated during molecule setup.

Performance Benchmarking Setup. Performance benchmarking for ROCS and the present invention was run on a Mac Pro with 2×3 GHz Quad-Core Intel Xeon CPUs (Core 2 architecture) and 16 GB of DDR2 667 MHz fully buffered memory, running OS X 10.5.8. Both the ROCS and present invention benchmarking scripts were written in Python and executed on a 32-bit build of CPython 2.5.2. All benchmarks were conducted as single-CPU tests.

ROCS was called from within a Python script using the OpenEye OEShape toolkit, and greater than 97% of the execution time was spent inside the OEBestOverlay.Overlay function (which calculates the optimal overlap).

Operations of the present invention, other than Tanimoto calculations, were performed using standard operations in Numpy 1.1.0, as downloaded in binary form from numpy.scipy.org. The C module for Tanimoto calculation according to the present invention was built against GotoBLAS2 1.13, using gcc 4.0.1 with the following performance-relevant compiler options: g++-arch i386-fnostrict-aliasing-Wno-long-double-no-cpp-precomp-fno-common-DNDEBUG-msse-msse2-msse3-march=core2-mfpmath=sse-O3. Tanimoto calculation times for the present invention were computed over 4096×262,144 Tanimotos, calculated in blocks of 4096×32,768, in 64 dimensions.

The present invention is not limited to performing molecular similarity calculations. Instead, the present invention can be generally applied to situations where similarities may exist and where similarity measures are or can be calculated, for example, using Tanimotos as discussed herein. For example, the teachings of the present invention can be used in applications for string searches or data mining.

It should be appreciated by those skilled in the art that the specific embodiments disclosed above may be readily utilized as a basis for modifying or designing other similarity measuring algorithms. It should also be appreciated by those skilled in the art that such modifications do not depart from the scope of the invention as set forth in the appended claims.

What is claimed is:

1. A computer-implemented method for estimating similarities comprising:
   receiving, by a computer, a set of data;
   dividing, by the computer, the set of data into a first subset and a second subset, wherein the second subset is larger than the first subset;
   computing, by the computer, similarity calculations for each element of the second subset and the elements of the first subset;
   computing, by the computer, an approximation matrix from the computed similarity calculations;
   generating, by the computer, a similarity measure for a query element based on the approximation matrix.

2. The method of claim 1, wherein the set of data includes chemical molecular data.

3. The method of claim 1, further comprising computing, by the computer, similarity calculations for pairs of the first subset.

4. The method of claim 3, wherein correction factors are applied to the similarity calculations for pairs of the first subset.

5. The method of claim 3, further comprising converting, by the computer, results of the similarity calculations to an inner product matrix of the first subset.

6. The method of claim 5, further comprising diagonalizing, by the computer, the first subset inner product matrix to generate a vector approximation of the first subset.

7. The method of claim 1, further comprising converting, by the computer, results of the similarity calculations to an inner product matrix of the second subset.

8. The method of claim 7, further comprising generating, by the computer, a vector approximation of the second subset.

9. The method of claim 8, wherein the second subset vector approximation is computed by a least squares method.

10. The method of claim 1, wherein the approximation matrix is further computed from a first subset vector approximation and a second subset vector approximation.

11. The method of claim 1, wherein the set of data includes text data.

12. A method for estimating similarities comprising:
   receiving, by a computer, a set of data;
   dividing, by the computer, the set of data into a first subset and a second subset, wherein the second subset is larger than the first subset;
   computing, by the computer, a first subset vector approximation;
   computing, by the computer, a second subset vector approximation; and
   computing, by the computer, a query for a first element of the second subset against the first subset vector approximation.

13. The method of claim 12, wherein the set of data includes chemical molecular data.

14. The method of claim 12, further comprising computing, by the computer, similarity calculations for pairs of the first subset.

15. The method of claim 14, wherein correction factors are applied to the similarity calculations for pairs of the first subset.

16. The method of claim 14, further comprising converting, by the computer, results of the similarity calculations to a first subset inner product matrix.

17. The method of claim 16, further comprising diagonolizing, by the computer, the first subset inner product matrix to generate the first subset vector approximation.

18. The method of claim 12, further comprising computing, by the computer, similarity calculations for the first subset and converting its results to a second subset inner product matrix.

19. The method of claim 18, wherein the second subset vector approximation is generated from the second subset inner product matrix.

20. The method of claim 12, wherein the second subset vector approximation is computed by a least squares method.

21. The method of claim 12, further comprising computing, by the computer, an approximation matrix from the first subset vector approximation and the second subset vector approximation.

22. The method of claim 12, wherein the set of data includes text data.

* * * * *